US00PP31140P2

(12) United States Plant Patent
Westhoff

(10) Patent No.: US PP31,140 P2
(45) Date of Patent: Nov. 26, 2019

(54) ***CALIBRACHOA* PLANT NAMED 'WESCACANBOUN'**

(50) Latin Name: ***Calibrachoa* sp.**
Varietal Denomination: Wescacanboun

(71) Applicant: Heinrich Westhoff, Sudlohn (DE)

(72) Inventor: Heinrich Westhoff, Sudlohn (DE)

(73) Assignee: Gartenbau und Spezialkulturen Westhoff GbR, Sudlohn (DE)

( * ) Notice: Subject to any disclaimer, the term of this patent is extended or adjusted under 35 U.S.C. 154(b) by 0 days.

(21) Appl. No.: 15/999,969

(22) Filed: Sep. 4, 2018

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 6/821
See application file for complete search history.

*Primary Examiner* — Keith O. Robinson
(74) *Attorney, Agent, or Firm* — C. A. Whealy

(57) ABSTRACT

A new and distinct cultivar of *Calibrachoa* plant named 'Wescacanboun', characterized by its compact, semi-upright and mounding growth habit; moderately vigorous growth habit; freely branching habit; freely flowering habit; large flowers that have star-shaped patterns that are yellow orange and red purple in color; and good garden performance.

3 Drawing Sheets

Botanical designation: *Calibrachoa* sp.
Cultivar denomination: 'WESCACANBOUN'.

BACKGROUND OF THE INVENTION

The present invention relates to a new and distinct cultivar of *Calibrachoa* plant, botanically known as *Calibrachoa* sp. and hereinafter referred to by the name 'Wescacanboun'.

The new *Calibrachoa* plant is a product of a planned breeding program conducted by the Inventor in Südlohn, Germany. The objective of the breeding program is to create new compact *Calibrachoa* plants with uniform plant habit and numerous attractive and uniquely-colored flowers.

The new *Calibrachoa* plant originated from a cross-pollination made by the Inventor in the summer of 2016 in Südlohn, Germany of a proprietary selection of *Calibrachoa* sp. identified as code number 16P383G, not patented, as the female, or seed, parent with a proprietary selection of *Calibrachoa* sp. identified as code number 16P55X, not patented, as the male, or pollen, parent. The new *Calibrachoa* plant was discovered and selected by the Inventor as a single flowering plant within the progeny of the stated cross-pollination in a controlled environment in Südlohn, Germany in April, 2017.

Asexual reproduction of the new *Calibrachoa* plant by vegetative cuttings in a controlled greenhouse environment in Südlohn, Germany since April, 2017 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Wescacanboun'. These characteristics in combination distinguish 'Wescacanboun' as a new and distinct *Calibrachoa* plant:

1. Compact, semi-upright and mounding growth habit.
2. Moderately vigorous growth habit.
3. Freely branching habit.
4. Freely flowering habit.
5. Large flowers that have star-shaped patterns that are yellow orange and red purple in color; the varying amounts of yellow orange and red purple coloration is dependent on environmental conditions and developmental stage of the flowers.
6. Good garden performance.

Plants of the new *Calibrachoa* can be compared to plants of the female parent selection. Plants of the new *Calibrachoa* differ primarily from plants of the female parent selection in the following characteristics:

1. Plants of the new *Calibrachoa* are more compact than plants of the female parent selection.
2. Plants of the new *Calibrachoa* are more freely branching than plants of the female parent selection.
3. Plants of the new *Calibrachoa* and the female parent selection differ in flower color as plants of the female parent selection have deep yellow-colored flowers.

Plants of the new *Calibrachoa* can be compared to plants of the male parent selection. Plants of the new *Calibrachoa* differ primarily from plants of the male parent selection in the following characteristics:

1. Plants of the new *Calibrachoa* are more freely flowering than plants of the male parent selection.
2. Plants of the new *Calibrachoa* and the male parent selection differ in flower color as plants of the new *Calibrachoa* have yellow orange and red purple-colored flowers whereas plants of the male parent selection have light yellow and pink purple-colored flowers.

Plants of the new *Calibrachoa* can be compared to plants of the *Calibrachoa* sp. 'Wescacandy', disclosed in U.S. Plant Pat. No. 26,272. In side-by-side comparisons, plants of the new *Calibrachoa* differ from plants of 'Wescacandy' in the following characteristics:

1. Plants of the new *Calibrachoa* are more vigorous and faster growing than plants of 'Wescacandy'.
2. Plants of the new *Calibrachoa* are more freely branching than plants of 'Wescacandy'.
3. Plants of the new *Calibrachoa* are more freely flowering than plants of 'Wescacandy'.
4. Plants of the new *Calibrachoa* have larger flowers than plants of 'Wescacandy'.
5. Plants of the new *Calibrachoa* and 'Wescacandy' differ in flower color as plants of as plants of the new *Calibrachoa* have yellow orange and red purple-colored flowers whereas plants of 'Wescacandy' have lighter yellow and red purple-colored flowers.

Plants of the new *Calibrachoa* can also be compared to plants of the *Calibrachoa* sp. 'Wescain', disclosed in U.S. Plant Pat. No. 21,658. In side-by-side comparisons, plants of the new *Calibrachoa* differ from plants of 'Wescain' in the following characteristics:

1. Plants of the new *Calibrachoa* are more mounding than and not as flattened as than plants of 'Wescain'.
2. Plants of the new *Calibrachoa* have smaller leaves than plants of 'Wescain'.
3. Plants of the new *Calibrachoa* and 'Wescain' differ in flower color as plants of as plants of the new *Calibrachoa* have yellow orange and red purple-colored flowers whereas plants of 'Wescain' have purple violet-colored flowers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet comprises a side perspective view of a typical flowering plant of 'Wescacanboun' grown in a container.

The photograph on the second sheet is a close-up view of typical flowers of 'Wescacanboun' showing the flower color variations of 'Wescacanboun'.

The photograph on the third sheet is a close-up view of typical flowers of 'Wescacanboun' (left) and 'Wescacandy' (right).

DETAILED BOTANICAL DESCRIPTION

The aforementioned photographs and following observations, measurements and values describe plants grown in 12-cm containers in Südlohn, Germany, under typical commercial cultural practices during the late spring in a glass-covered greenhouse with day temperatures ranging from 23° C. to 27° C., night temperatures ranging from 16° C. to 18° C. and light levels ranging from 3 to 50 klux. Plants were pinched two times and were 13 weeks old when the photographs and description were taken. In the following description, color references are made to The Royal Horticultural Society Colour Chart, 2001 Edition, except where general terms of ordinary dictionary significance are used.

Botanical classification: *Calibrachoa* sp. 'Wescacanboun'.

Parentage:

*Female, or seed, parent*.—Proprietary selection of *Calibrachoa* sp. identified as code number 16P383G, not patented.

*Male, or pollen, parent*.—Proprietary selection of *Calibrachoa* sp. identified as code number 16P55X, not patented.

Propagation:

*Type*.—By vegetative tip cuttings.

*Time to initiate roots, summer*.—About 14 to 20 days at temperatures about 18° C. to 20° C.

*Time to initiate roots, winter*.—About 21 to 24 days at temperatures about 18° C. to 20° C.

*Time to produce a rooted young plant, summer*.—About three to four weeks at temperatures about 18° C. to 20° C.

*Time to produce a rooted young plant, winter*.—About four to five weeks at temperatures about 18° C. to 20° C.

*Root description*.—Fibrous, medium in thickness; color, close to 158A.

*Rooting habit*.—Freely branching; moderately dense to dense.

Plant description:

*Plant and growth habit*.—Compact, semi-upright to mounding growth habit; freely branching habit with lateral branches potentially developing at every node; moderately vigorous growth habit; moderate growth rate.

*Plant height*.—About 15 cm to 17 cm.

*Plant diameter*.—About 33 cm.

Lateral branch description:

*Length*.—About 12 cm.

*Diameter*.—About 1 mm.

*Internode length*.—About 8 mm.

*Strength*.—Strong; flexible.

*Aspect*.—Initially upright to outwardly spreading.

*Texture*.—Pubescent.

*Color*.—Close to 146C.

Leaf description:

*Arrangement*.—Alternate, simple; sessile.

*Length*.—About 2.5 cm to 3 cm.

*Width*.—About 1 cm.

*Shape*.—Oblanceolate.

*Apex*.—Obtuse.

*Base*.—Attenuate.

*Margin*.—Entire.

*Texture and luster, upper surface*.—Sparsely pubescent; matte.

*Texture and luster, upper surface*.—Densely pubescent; matte.

*Venation pattern*.—Pinnate.

*Color*.—Developing leaves, upper surface: Close to 146A. Developing leaves, lower surface: Close to 146B. Fully expanded leaves, upper and lower surfaces: Close to 147B; venation, close to 147C.

Flower description:

*Flower arrangement and habit*.—Single salverform flowers arising from leaf axils; freely flowering habit with numerous flowers developing per plant; flowers face mostly outwardly.

*Fragrance*.—None detected.

*Natural flowering season*.—Plants flower continuously from April until autumn in Germany.

*Flower longevity*.—Individual flowers last about a week on the plant; flowers not persistent.

*Flower diameter*.—About 3.6 cm.

*Flower length* (*height*).—About 2.2 cm.

*Flower buds*.—Length: About 2.1 cm. Diameter: About 5 mm. Shape: Oblong. Color: Towards the base, close to 11A; mid-section, close to 11 A with venation, close to 176A; towards the apex, close to 11A with speckles, close to 176A.

*Corolla*.—Arrangement: Five petals fused at the base and opening into a flared trumpet. Petal length from throat: About 1.3 cm. Petal lobe width: About 1.7 cm. Petal shape: Roughly semi-circular. Petal apex: Obtuse to slightly cuspidate. Petal margin: Entire. Petal texture, upper and lower surfaces: Smooth, glabrous; slightly satiny; matte. Color: When opening, upper surface: Star-shaped patterns, close to 13A and N57A; the amount of yellow orange and red purple coloration varies with environmental conditions and developmental stage of the flowers. When opening, lower surface: Star-shaped patterns, close to 10C and 63B; the amount of yellow and red purple coloration varies with environmental conditions and developmental stage of the flowers. Fully opened, upper surface: Star-shaped patterns, close to 15A to 15C and N66B to N66C; the amount of yellow orange and red purple coloration varies with environmental conditions and developmental stage of the flowers; red purple color becoming closer to 67B with development. Fully opened, lower surface: Star-shaped patterns, close to 15D and 63C; the amount of yellow orange and red purple coloration varies with environmental conditions and developmental stage of the flowers; colors becoming closer to N74C and 18C with development.

*Calyx*.—Arrangement: One star-shaped calyx tube with five sepals fused at the base per flower. Sepal length: About 1.4 cm. Sepal width: About 4 mm. Sepal shape: Lanceolate. Sepal apex: Obtuse. Sepal margin: Entire. Sepal texture and luster, upper and lower surfaces: Smooth, glabrous; matte. Color, upper and lower surfaces: Close to 146A to 146C.

*Peduncles*.—Length: About 1.3 cm. Diameter: About 1 mm. Strength: Moderately strong; flexible. Texture and luster: Pubescent; matte. Color: Close to 144A.

*Reproductive organs*.—Stamens: Quantity: About five per flower. Filament length: About 5 mm to 8 mm. Filament color: Close to 145C. Anther shape: Ovate, four-parted. Anther length: About 1 mm. Anther color: Close to 8A. Pollen amount: Abundant. Pollen color: Close to 8A. Pistils: Quantity: One per flower. Pistil length: About 8 mm. Style length: About 7 mm. Style color: Close to 144C to 144D. Stigma shape: Ovate; two-parted. Stigma color: Close to 144A. Ovary color: Close to 144C. Fruits and seeds: To date, fruit and seed development has not been observed on plants of the new *Calibrachoa*.

Garden performance: Plants of the new *Calibrachoa* have been observed to have good garden performance and tolerate wind, rain and temperatures ranging from about 16° C. to about 28° C.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'Wescacanboun' as illustrated and described.

* * * * *

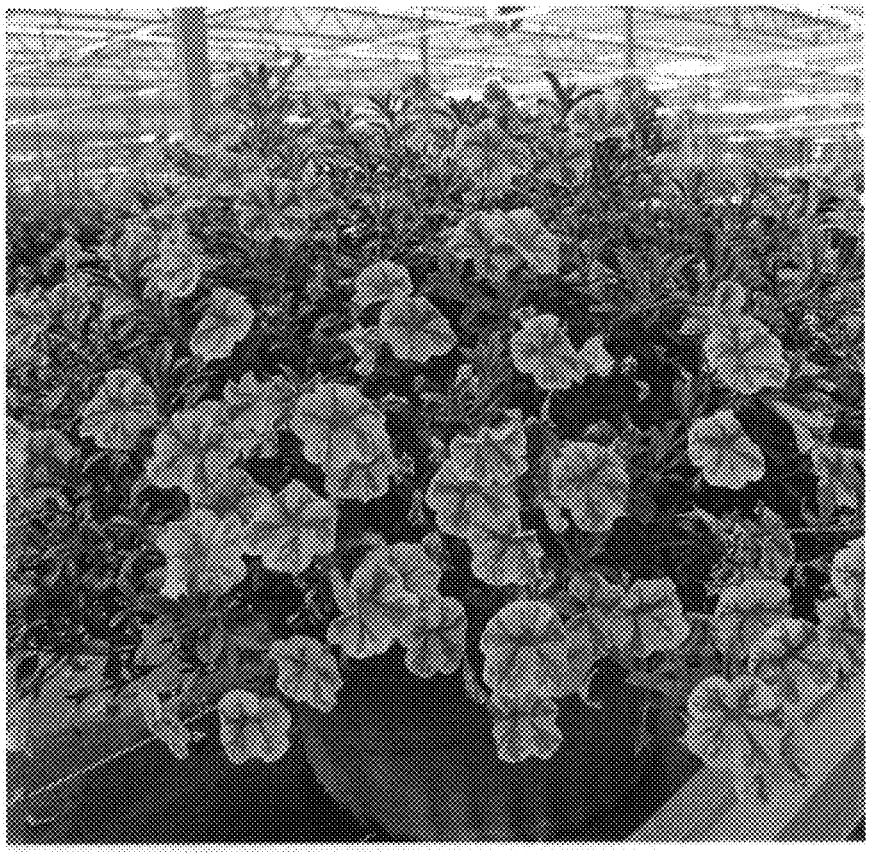

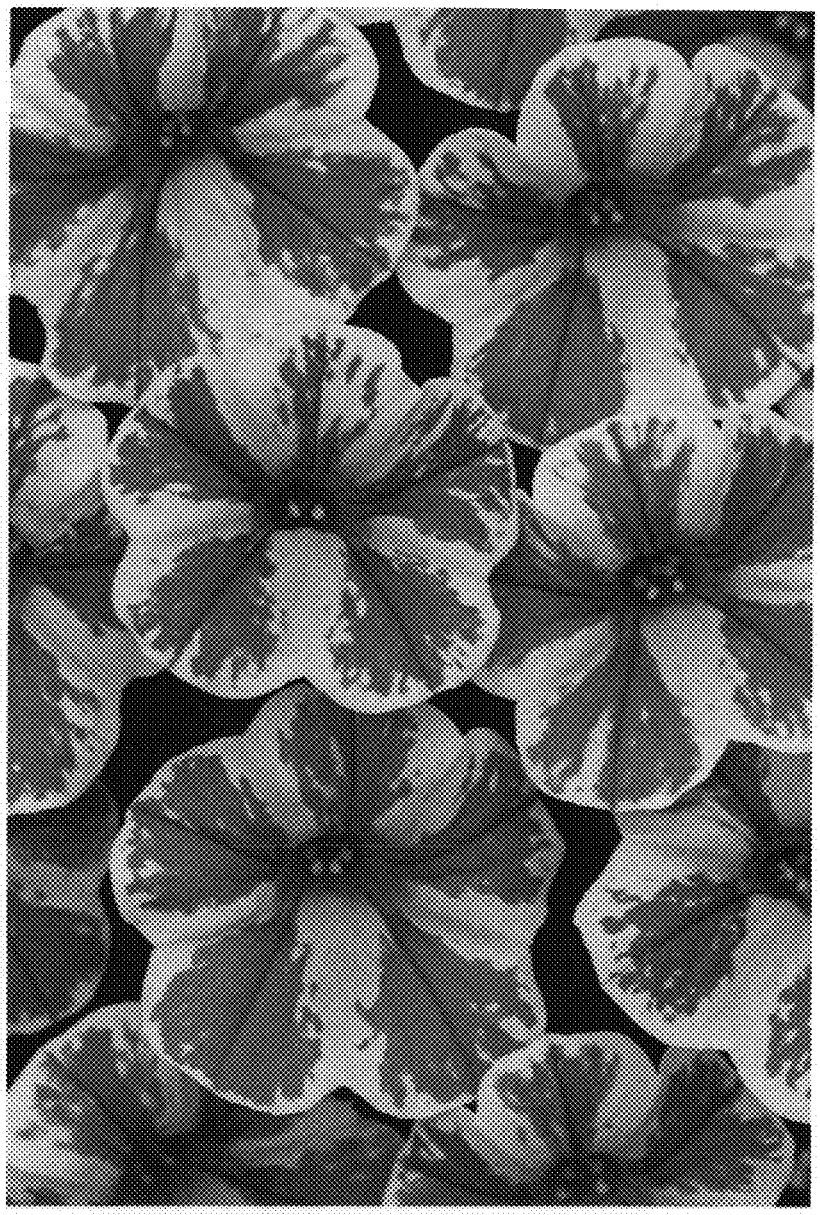

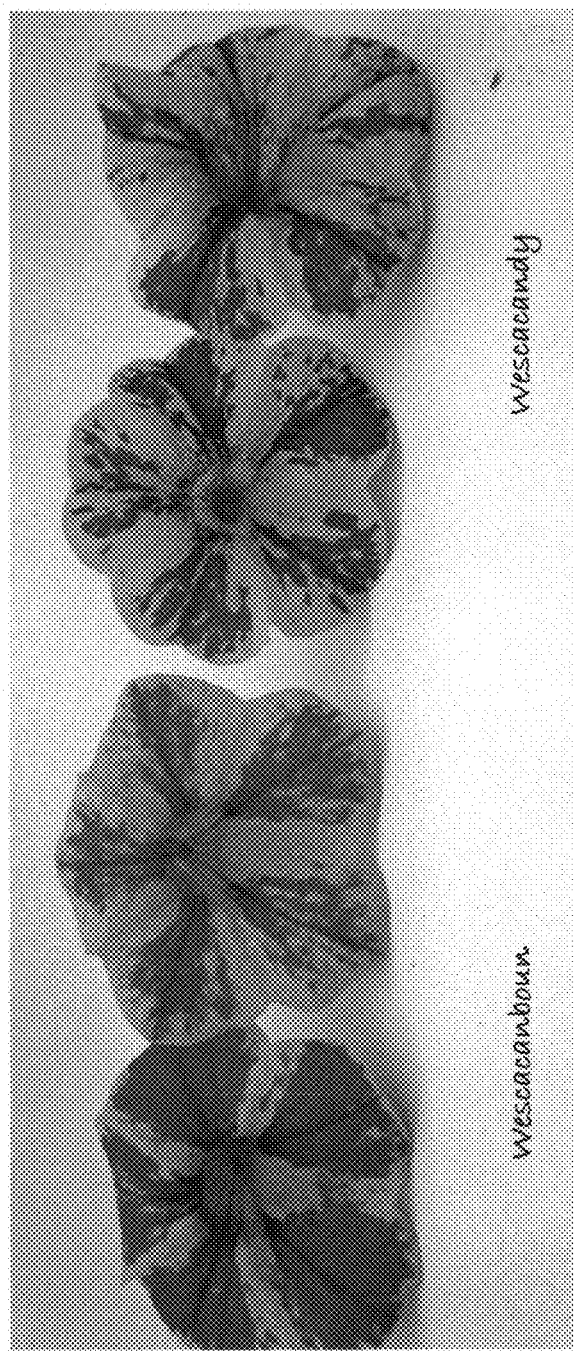
Wescandy
Wescantown